(12) United States Patent
Ichige et al.

(10) Patent No.: US 9,417,142 B2
(45) Date of Patent: Aug. 16, 2016

(54) AXIAL FORCE SENSOR

(71) Applicant: A&D Company Limited, Tokyo (JP)

(72) Inventors: Tatsuo Ichige, Kitamoto (JP); Masaaki Banno, Kitamoto (JP); Tomoyuki Ishimori, Kitamoto (JP)

(73) Assignee: A&D Company, Limited, Tokyo (JP)

( * ) Notice: Subject to any disclaimer, the term of this patent is extended or adjusted under 35 U.S.C. 154(b) by 43 days.

(21) Appl. No.: 14/401,167

(22) PCT Filed: Apr. 30, 2013

(86) PCT No.: PCT/JP2013/062542
§ 371 (c)(1),
(2) Date: Nov. 14, 2014

(87) PCT Pub. No.: WO2013/172191
PCT Pub. Date: Nov. 21, 2013

(65) Prior Publication Data
US 2015/0128725 A1     May 14, 2015

(30) Foreign Application Priority Data

May 16, 2012   (JP) ................................ 2012-112293

(51) Int. Cl.
| | |
|---|---|
| *G01L 1/22* | (2006.01) |
| *G01L 1/24* | (2006.01) |
| *G01N 3/08* | (2006.01) |

(52) U.S. Cl.
CPC .................. *G01L 1/22* (2013.01); *G01L 1/2231* (2013.01); *G01L 1/246* (2013.01); *G01N 3/08* (2013.01)

(58) Field of Classification Search
CPC ........... G01L 1/22; G01L 1/2231; G01N 3/08

USPC ...................... 73/862.041–862.046
See application file for complete search history.

(56) References Cited

U.S. PATENT DOCUMENTS 3,151,258 A     9/1964   Sonderegger et al.
4,175,445 A * 11/1979   Templeton, III ........ G01W 1/00
                                                                                73/726

(Continued)

FOREIGN PATENT DOCUMENTS

| GB | 2326719 | 12/1998 |
|---|---|---|
| JP | 2003-083820 | 3/2003 |

(Continued)

OTHER PUBLICATIONS

International Search Report PCT/JP2013/062542 dated Jun. 11, 2013.

*Primary Examiner* — Max Noori
(74) *Attorney, Agent, or Firm* — Roberts Mlotkowski Safran Cole & Calderon, PC

(57) ABSTRACT

A low-cost, compact, high-precision axial force sensor is provided. The axial force sensor includes a pair of parallel pressing plates and a strain gauge sandwiched therebetween. The strain gauge includes a plurality of strain-sensitive resistive elements around its periphery, and is provided with a spacer that transmits a pressing force from the pressing plates to some of the strain-sensitive elements but blocks the pressing force to the rest of the strain-sensitive elements. The output signal of the strain-sensitive elements blocked from the pressing force provide an accurate baseline to compare the output signal of the strain-elements subjected to the pressing force. The spacer has a uniform pattern of open and closed portions. On the strain gauge, the strain-sensitive elements are provided at both the open and closed portions of the spacer.

3 Claims, 3 Drawing Sheets

(56) References Cited

U.S. PATENT DOCUMENTS

| | | | |
|---|---|---|---|
| 5,222,399 A | 6/1993 | Kropp | |
| 5,447,074 A * | 9/1995 | Polaert | G01L 1/2206 73/763 |
| 2011/0226069 A1 * | 9/2011 | Kim | G01L 1/2293 73/862.045 |
| 2012/0198945 A1 * | 8/2012 | Yoneyama | B25J 13/083 73/862.042 |
| 2013/0139615 A1 * | 6/2013 | Kwom | G01L 5/161 73/862.045 |
| 2013/0213147 A1 * | 8/2013 | Rice | G01L 1/20 73/862.046 |

FOREIGN PATENT DOCUMENTS

| | | |
|---|---|---|
| JP | 2009-014609 | 1/2009 |
| JP | 2010-197276 | 9/2010 |
| JP | 2011-080586 | 4/2011 |

* cited by examiner

AXIAL FORCE SENSOR

TECHNICAL FIELD

The present invention relates to an axial force sensor, and particularly concerns an axial force sensor to be used in bolt tightening management and a suspension axial force measurement device and the like.

BACKGROUND ART

Tightening management of bolts, screws, etc., has been commonly performed by managing torque when tightening. However, for preventing these from loosening, it is desired to directly measure tightening axial force rather than the tightening torque for management, and axial force sensors are therefore required.

Axial force sensors have other uses such as suspension test apparatuses and electric disk brakes. For example, Patent Literature 1 describes an axial force sensor to be used for an electric disk brake. This axial force sensor is configured with a pair of pressing plates and a plurality of crystal piezoelectric elements held sandwiched by the pair of pressing plates, and can, when a compressive force is applied to the pair of pressure plates, detect an axial force thereof by the crystal piezoelectric elements.

Also, Patent Literature 2 describes a suspension axial force measurement apparatus. For this axial force measurement apparatus, an axial force measuring section is provided over a suspension, and the suspension is supported by a mount via the axial force measuring section. As the axial force measuring section, a 6-component dynamometer is used, so that an axial force of the suspension can be measured as six forces components.

CITATION LIST

Patent Literature

Patent Literature 1: Japanese Published Unexamined Patent Application No. 2011-80586
Patent Literature 2: Japanese Published Unexamined Patent Application No. 2010-197276

SUMMARY OF INVENTION

Technical Problem

Meanwhile, axial force sensors are roughly divided into ones using piezoelectric elements, ones using strain gauges, and ones that use ultrasonic waves. The ones using piezoelectric elements and the ones that use ultrasonic waves have a problem that the costs are very expensive. On the other hand, the ones using strain gauges are low cost, but have a problem of bulk thickness. When described specifically, for the conventional axial force sensor using a strain gauge, it has been necessary because of its configuration to have the strain gauge attached to a part to be deformed, so that the strain gauge has been arranged parallel to its measurement direction. For this reason, there has been a problem that the axial force sensor has a thickness greater by at least the size of the strain gauge, and is thereby increased in size.

The present invention has been made in view of such circumstances, and an object thereof is to provide a low-cost, compact, high-precision axial force sensor.

Solution to Problem

In order to achieve the above-mentioned object, a first aspect of the invention provides an axial force sensor configured including a pair of pressing plates and a strain gauge arranged in parallel, and sandwiching the strain gauge with the pair of pressing plates.

The axial force sensor of the present invention has a sandwiched structure in which the strain gauge is sandwiched between the pair of pressing plates, and is very thin. According to this axial force sensor, when the pair of pressing plates are pressed from both sides, because the strain gauge is pressed to be deformed, the pressing force can be detected by detecting a change in resistance value of a sensitive element. In addition, for the conventional axial force sensor using a strain gauge, the strain gauge is arranged parallel to its measurement direction, whereas for the axial force sensor of the present invention, the strain gauge is disposed parallel to the pressing plates (that is, in a direction orthogonal to the measurement direction), and can thus be made very thin.

A second aspect of the invention is the first aspect of the invention, in which the strain gauge includes a plurality of sensitive elements consisting of resistors, and is provided with a transmitting and blocking mechanism that transmits a pressing force from the pair of pressing plates to at least one of the plurality of sensitive elements and blocks the pressing force with respect to the rest of the sensitive elements.

According to the present invention, when the pair of pressing plates are pressed, the pressing force is transmitted to a part of the sensitive elements, and the pressing force is not transmitted to the rest of the sensitive elements. In the sensitive element to which the pressing force is transmitted, various forces (e.g., forces including a bending stress and the like) including the pressing force are detected, and forces other than the pressing force are detected in the sensitive element to which the pressing force is not transmitted. Thus, by using a difference in detection values between the two types of sensitive elements, only the pressing force can be determined. In addition, the axial force sensor having a sandwiched structure in which the strain gauge is sandwiched with the pair of pressing plates has a drawback that it is easily affected by forces other than a pressing force, and the precision of measuring the pressing force easily degrades, but according to the present invention, the forces other than a pressing force can cancel each other out, so that the pressing force can be measured at high precision.

A third aspect of the invention is the second aspect of the invention, in which the transmitting and blocking mechanism is a plate-like spacer having an opening portion, and is arranged between the pair of pressing plates together with the strain gauge, and the sensitive elements of the strain gauge are respectively arranged at a position where the spacer makes contact and a position of the opening portion.

According to the present invention, a pressing force is transmitted to the sensitive element at the position where the spacer makes contact and the pressing force is blocked with respect to the sensitive element at the position of the opening portion. Thus, the pressing force can be detected based on a difference in detection values between the two types of sensitive elements. Also, according to the present invention, the axial force sensor has a sandwiched structure in which the plate-like spacer is sandwiched together with the strain gauge between the pair of pressing plates, and is very thin.

A fourth aspect of the invention is the third aspect of the invention, in which the spacer is formed in a ring shape, and has the opening portions arranged at constant angular intervals in a circumferential direction, and the strain gauge has the sensitive elements arranged at constant angular intervals at positions of the opening portions and between the opening portions at constant angular intervals.

According to the present invention, the sensitive elements to which a pressing force is transmitted and the sensitive elements with respect to which the pressing force is blocked are arranged alternately at constant angular intervals. Thus, forces other than an axial force can reliably cancel each other out, and the axial force at a center position can be precisely measured.

A fifth aspect of the invention is any one of the first to fourth aspects of the invention, in which a Wheatstone bridge circuit is formed for which the sensitive elements to which a pressing force is transmitted are arranged on opposite sides to each other and the sensitive elements with respect to which the pressing force is blocked are arranged on opposite sides to each other. According to the present invention, forces other than an axial force cancel each other out, and only the axial force can be detected.

Advantageous Effects of Invention

According to the axial force sensor of the present invention, which has a sandwiched structure in which the strain gauge is sandwiched between the pair of pressing plates, when the pair of pressing plates are pressed from both sides, because the strain gauge is pressed to be deformed, the pressing force can be detected by detecting a change in resistance value of the sensitive element.

DESCRIPTION OF EMBODIMENTS

Figure 1:
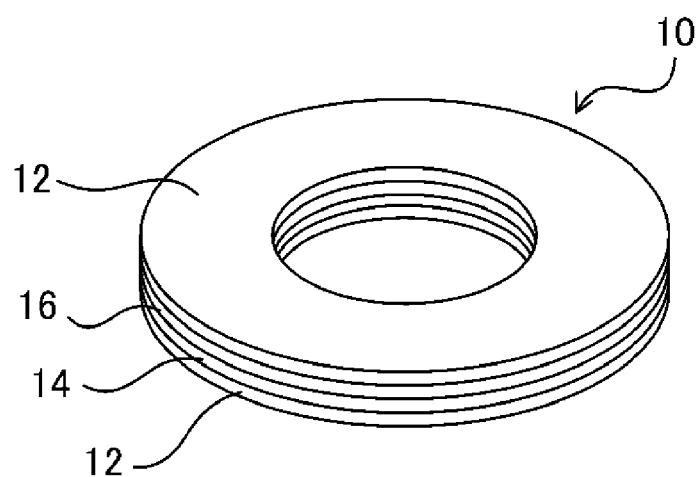
FIG. 1 is a perspective view showing an axial force sensor of the present embodiment.
Figure 2:
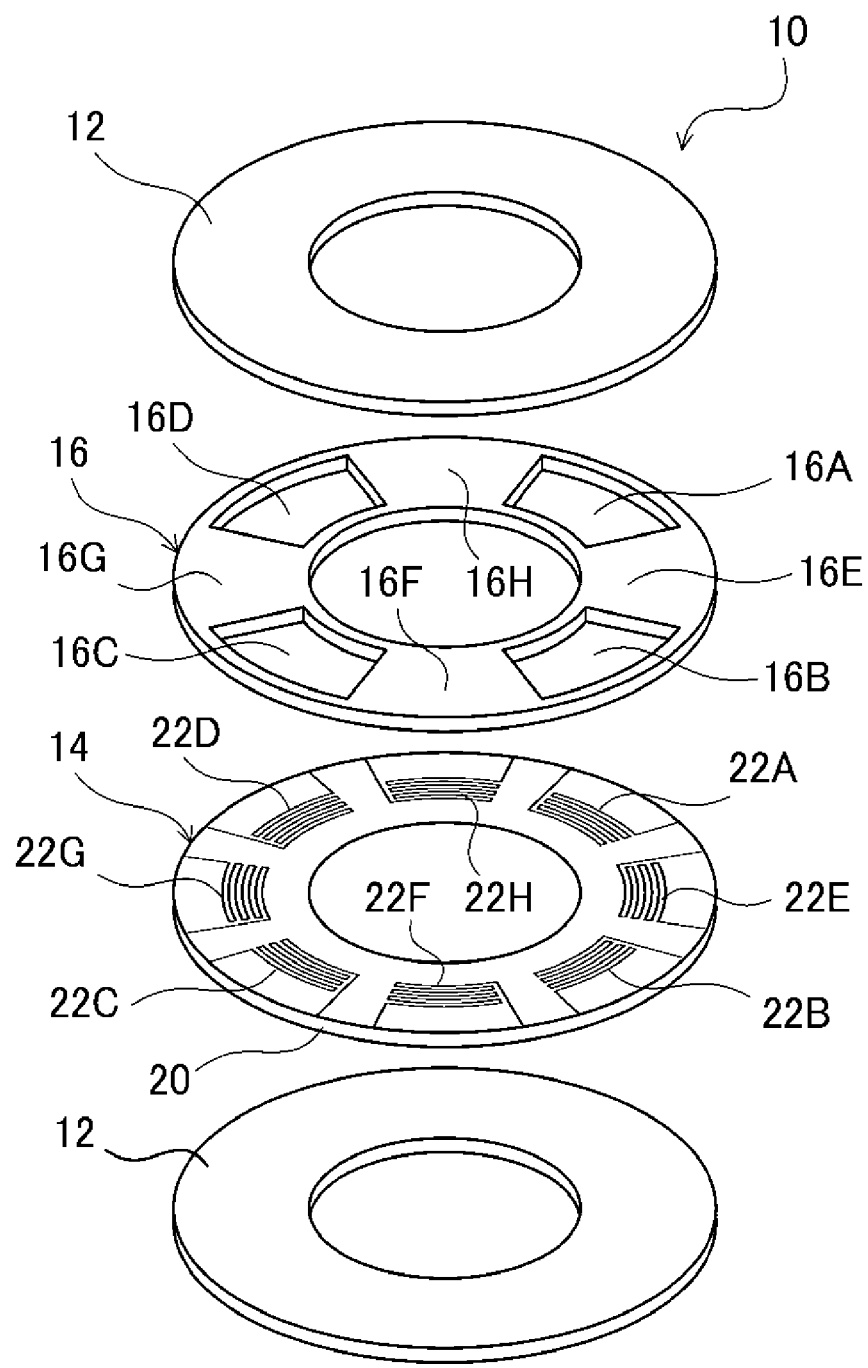
FIG. 2 is an exploded perspective view showing a configuration of the axial force sensor in FIG. 1.
Figure 3:
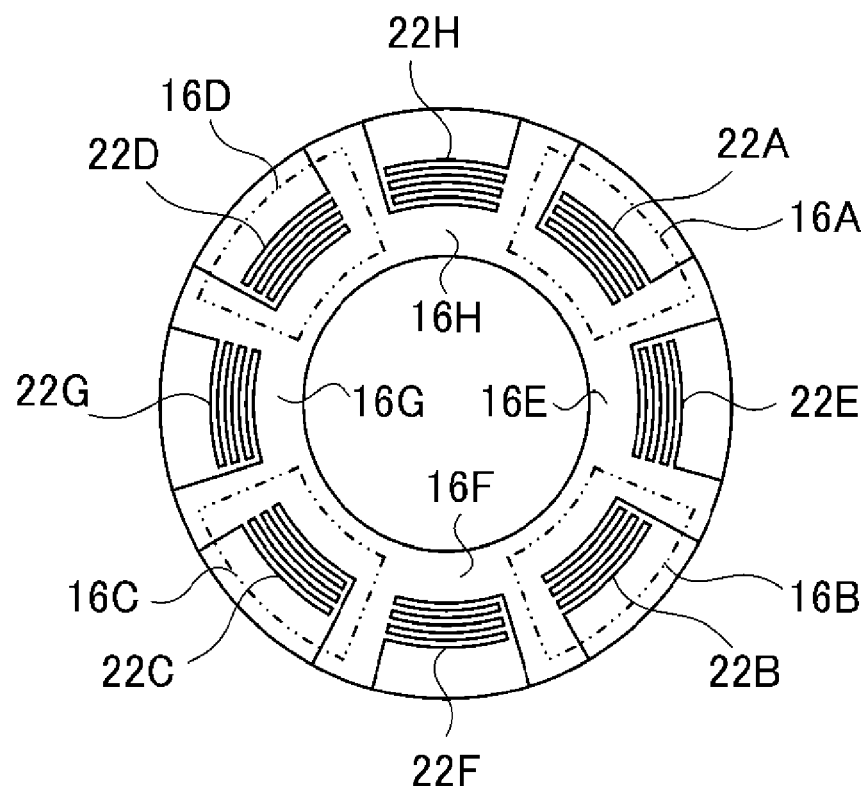
FIG. 3 is a view showing an arrangement of the strain gauge in FIG. 1.

Hereinafter, preferred embodiments of an axial force sensor according to the present invention will be described in accordance with the accompanying drawings. FIG. 1 is a perspective view showing an axial force sensor 10 applied with the present invention, and FIG. 2 is an exploded perspective view showing an internal configuration of the axial force sensor 10. FIG. 3 is a plan view of a strain gauge 14, and shows the positions of opening portions 16A to 16D and pressing portions 16E to 16H in a spacer 16.

As shown in these figures, the axial force sensor 10 is configured with the pair of pressing plates 12, the strain gauge 14, and the spacer 16, and has a sandwiched structure in which the strain gauge 14 and the spacer 16 are sandwiched with the pair of pressing plates 12.

The pressing plate 12 is formed of a metal plate such as stainless steel in a ring shape. It suffices to set the size of the pressing plate 12 according to the measuring object, and for example, in the case of a use for tightening management of bolts etc., the inner diameter of the pressing plate is set to such a size so as to allow insertion therethrough of a shaft part of the bolt.

The spacer 16 is formed of a metal plate such as stainless steel in a ring shape. The material of the spacer 16 is not particularly limited, but for preventing the occurrence of an unnecessary strain or stress by the spacer 16, a spacer of the same material as that of the pressing plates 12 is preferably used. Similarly, the size (inner diameter, outer diameter, thickness) of the spacer 16 is not particularly limited, but for preventing the occurrence of an unnecessary strain or stress by the spacer 16, the spacer 16 is preferably designed similarly to the pressing plate 12. Because the spacer 16 accordingly has substantially the same characteristics as those of the pressing plate 12, the occurrence of an unnecessary strain or stress can be suppressed. In addition, the pressing plate 12 and the spacer 16 are separated from each other in the present embodiment, but the present invention is not limited thereto, and unevenness may be formed on the back surface of the pressing plate 12 in place of providing the spacer 16. Also, in the present embodiment, the single spacer 16 is provided on one side of the strain gauge 14, but two spacers 16 may be provided on both sides of the strain gauge 14.

In the spacer 16, four opening portions 16A, 16B, 16C, and 16D are formed in a manner of penetrating from the front to back surfaces. The four opening portions 16A to 16D are arranged at equal intervals (90 degree intervals), and formed, as their sizes (angles), with angles (approximately 45 degrees) for which the whole circumference is divided to be approximately ⅛. Thus, between the opening portions 16A to 16D, metal-plate parts (hereinafter, referred to as pressing portions) 16E, 16F, 16G, and 16H of the spacer 16 are arranged. The spacer 16 accordingly has, in its circumferential direction, the opening portions 16A to 16D and the pressing portions 16E to 16H arranged alternately at equal angular intervals.

The strain gauge 14 includes a base 20 formed in a ring shape, and on the base 20, eight sensitive elements 22A, 22B, 22C, 22D, 22E, 22F, 22G, and 22H called grids are provided. The base 20 is made of an insulating material such as a polyimide resin, and the sensitive elements 20A to 22H are formed of a metal foil having a thickness of a few microns adhered onto that base 20. The sensitive elements 20A to 22H have a pattern developed by multiple circumferentially arranged linear parts (gauge grids) connecting to other linear parts by folding tabs, and are connected to two connecting tabs arranged on the outer peripheral side. By connecting lead wires to the connecting tabs, a bridge circuit is formed as to be described later. In addition, a pattern so as to connect the respective sensitive elements 22A to 22H may be formed by a metal foil on the base 20. Also, the material of the base 20 and the sensitive element 22 is not particularly limited, and for example, a base 20 made of a polyvinyl resin or polyphenol resin may be used. Further, the pattern shape of the sensitive elements 22A to 22H is not limited to the above, and variously shaped patterns may be appropriately selected. An appropriate selection can be made from various patterns including, for example, a pattern for which multiple linear parts are radially arranged, and these linear parts are alternately connected by folding tabs on the inner peripheral side or outer peripheral side, and a pattern linear parts of which are formed in whorls.

As shown in FIG. 3, the sensitive elements 22A to 22H are arranged at constant angular intervals (that is, intervals of 45 degrees) in the circumferential direction. Also, the sensitive elements 22A to 22H are arranged at positions to overlap the opening portions 16A to 16D or the pressing portions 16E to 16H when the strain gauge 14 and the spacer 16 are stacked one on top of the other. Specifically, the sensitive elements 22A to 22D are arranged at positions to overlap the opening portions 16A to, respectively, and the sensitive elements 22E to 22H are arranged at the positions of the pressing portions 16E to 16H. In the case of such arrangement, in the sensitive elements 22A and 22D, because spaces (opening portions 16A to 16D) are arranged with respect to the pressing plate 12, a pressing force from the pressing plate 12 is blocked by the opening portions 16A to 16D, and is not transmitted to the sensitive elements 22A to 22D. On the other hand, in the sensitive elements 22E to 22H, because the pressing portions 16E to 16H of the spacer 16 are arranged with respect to the pressing plate 12, a pressing force from the pressing plate 12 is transmitted to the sensitive elements 22E to 22H.

Figure 4:
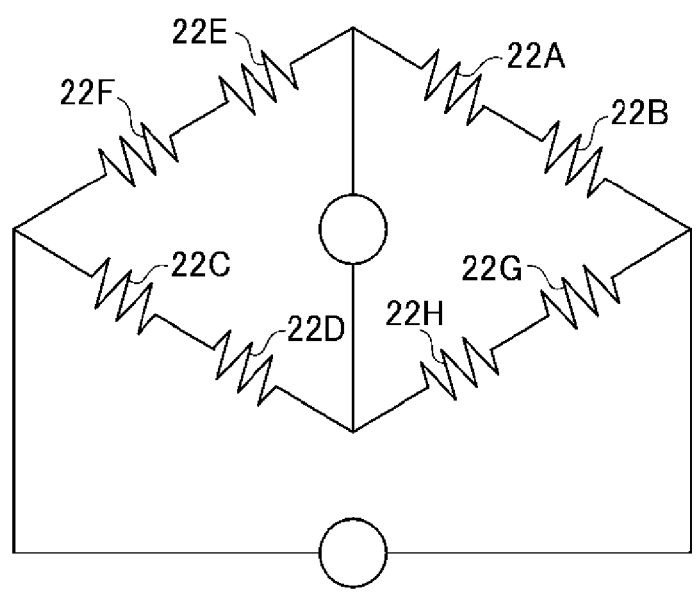
FIG. 4 is a circuit diagram of the strain gauge in FIG. 1.

FIG. 4 shows a circuit diagram of the strain gauge 14 in a simplified manner. As shown in the same figure, the sensitive elements 22A to 22H are connected so as to form a full-bridge circuit. Specifically, the sensitive elements 22A to 22D arranged at positions to overlap the opening portions 16A to 16D are arranged on opposite sides to each other and the sensitive elements 22E to 22H arranged at positions to overlap the pressing portions 16E to 16H are arranged on opposite sides to each other.

Next, the operation of the axial force sensor 10 configured as above will be described in an example of performing bolt tightening management.

First, a shaft portion of a bolt (not shown) is inserted through the axial force sensor 10. Then, the bolt is tightened to perform a measurement by the axial force sensor 10. As a result of the bolt being tightened, the pair of pressing plates 12 receives a force in the direction of pressure by sandwiching. This pressing force is transmitted to the sensitive elements 22E to 22H of the strain gauge 14 via the pressing portions 16E to 16H of the spacer 16. Thus, the sensitive elements 22E to 22H are changed in resistance values according to the pressing force. On the other hand, in the sensitive elements 22A to 22D arranged in the opening portions 16A to 16D, because the pressing force is blocked by the opening portions 16A to 16D, the pressing force is not transmitted. Thus, the sensitive elements 22A to 22D are not changed in resistance values depending on the pressing force.

Meanwhile, the sensitive elements 22A to 22H receive a force other than the pressing force, for example, a bending stress and the like, and are also changed in resistance values depending thereon. For example, when a large compressive force is applied to an outer peripheral portion of the pair of pressing plates 12, a large bending stress acts on an inner peripheral portion of the strain gauge 14, and the sensitive elements 22A to 22H may receive an influence greater than the compressive force.

Therefore, in the present embodiment, the sensitive elements 22E to 22H to which a pressing force is transmitted and the sensitive elements 22A to 22D to which a pressing force is not transmitted are provided, and a bridge circuit is formed with these sensitive elements. For this reason, influences other than the pressing force cancel each other out, so that only the pressing force is detected.

As such, according to the axial force sensor 10 of the present embodiment, despite a sandwiched structure in which the strain gauge 14 is sandwiched with the pressure plates 12, an axial force can be detected with high precision. Also, according to the present embodiment, because of being a sandwiched structure in which the strain gauge 14 and the spacer 16 are sandwiched with the pressing plates 12, the axial force sensor 10 is very thin, and compact.

In addition, eight sensitive elements 22A to 22H are provided for the embodiment described above, but the number of sensitive elements is not limited thereto. However, the larger the number of sensitive elements, the more precisely the influences other than the pressing force can cancel each other out. Also, the arrangement of the sensitive elements is not limited to the ones described above, but it is preferable to arrange sensitive elements to which a pressing force is transmitted and sensitive elements to which a pressing force is not transmitted, alternately at equal intervals.

Also, for the embodiment described above, the opening portions 16A to 16D are formed in substantially fan shapes surrounded by two concentric circles different in diameter and two radiuses, but the shape of the opening portions is not limited thereto, and it suffices that the spacer 16 is formed so as to become out of contact with the sensitive elements 22A and 22D. Thus, the shape of the opening portions may be, for example, a circular shape, an elliptic shape, a rectangular shape, and the like.

REFERENCE SIGNS LIST

10 . . . axial force sensor, 12 . . . pressing plate, 14 . . . strain gauge, 16 . . . spacer, 16E to 16H . . . pressing portion, 16A to 16D . . . opening portion, 20 . . . base, 22A to 22H . . . sensitive element

The invention claimed is:

1. An axial force sensor, comprising:
a pair of pressing plates;
a strain gauge arranged in parallel with, and sandwhiched between, the pair of pressing plates, the strain gauge having a plurality of strain-sensitive elements including resistors, and
a transmitting and blocking mechanism that transmits a pressing force from the pair of pressing plates to at least one of the plurality of strain-sensitive elements and blocks the pressing force from the rest of the strain-sensitive elements,
wherein the transmitting and blocking mechanism is a plate-like spacer arranged between the pair of pressing plates together with the strain gauge, the plate-like spacer having at least one open, force-blocking portion and at least one closed, force-transmitting portion; and
wherein one or more strain-sensitive elements of the strain gauge are respectively aligned with the at least one open, force-blocking portion and the at least one closed, force-transmitting portion.

2. The axial force sensor according to claim 1,
wherein the spacer is formed in a ring shape, and has a plurality of alternating open, force-blocking portions and closed, force-transmitting portions arranged at constant angular intervals in a circumferential direction, and
wherein the plurality of strain-sensitive elements of the strain gauge are arranged at constant angular intervals at positions corresponding to the open, force-blocking portions and positions of the closed, force-transmitting of the ring shaped spacer.

3. The axial force sensor according to claim 1, further comprising a Wheatstone bridge circuit wherein the strain-sensitive elements to which the pressing force is transmitted are arranged on opposite sides to each other and wherein the strain-sensitive elements to which the pressing force is blocked are arranged on opposite sides to each other.

* * * * *